United States Patent [19]

Nakata et al.

[11] Patent Number: 5,136,172
[45] Date of Patent: Aug. 4, 1992

[54] METHOD AND APPARATUS FOR DETECTING PHOTOACOUSTIC SIGNAL

[75] Inventors: Toshihiko Nakata, Hiratsuka; Yukio Kembo, Yokohama; Tsuguo Sawada, Tokyo; Takehiko Kitamori, Ushiku, all of Japan

[73] Assignee: Hitachi, Ltd., Tokyo, Japan

[21] Appl. No.: 567,319

[22] Filed: Aug. 14, 1990

[30] Foreign Application Priority Data

Aug. 16, 1989 [JP] Japan .................................. 1-210190

[51] Int. Cl.$^5$ ...................... G01N 21/88; G01N 21/25
[52] U.S. Cl. .................................. 250/572; 356/432; 73/602
[58] Field of Search ............ 250/572; 356/432, 432 T, 356/444, 445; 73/602; 364/553, 822, 825, 827

[56] References Cited

U.S. PATENT DOCUMENTS

| | | | |
|---|---|---|---|
| 3,885,224 | 5/1975 | Klahr ..................... | 73/602 |
| 4,052,889 | 10/1977 | Mucciardi et al. ..................... | 73/602 |
| 4,636,088 | 1/1987 | Rosencwaig et al. ........... | 356/432 T |
| 4,689,491 | 8/1987 | Lindow et al. ..................... | 250/572 |
| 4,854,710 | 8/1989 | Opsal et al. ......................... | 356/445 |

OTHER PUBLICATIONS

A. D. Poularikas et al., *Signals and Systems*, 1985, p. 242.
Masanori Hangyo, et al., "Photoacoustic Microscope", Department of Applied Physics, Faculty of Engineering OSAKA University, (Hihakai Kensa, Nondestructive Testing), vol. 36, No. 10, Oct. 1987, pp. 730–736.
P. Cielo, et al., "Laser Generation of Convergent Acoustic Waves and Applications to Materials Evaluation", IEEE 1986 Ultrasonics Symposium, pp. 515–526.

*Primary Examiner*—David C. Nelms
*Assistant Examiner*—J. Lee
*Attorney, Agent, or Firm*—Fay, Sharpe, Beall, Fagan, Minnich & McKee

[57] ABSTRACT

A method and apparatus are disclosed for detection of surface defects and internal defect information of a sample, such as a semiconductor device, using the photoacoustic effect. Operationally, an intensity-modulated laser beam is provided having a predetermined desired frequency. The intensity-modulated laser beam is focused on the sample thereby inducing said photoacoustic effect inside the sample which is detected in two-dimensional directions of the sample so as to compose a two-dimensional photoacoustic image of the excited sample. Surface and internal information of the sample is then extracted from the two-dimensional photoacoustic image and an inverse filtering factor is in turn computed on the basis of a thermal impulse response of the particular sample for compensating degradation of the resolution of the actual photoacoustic image obtained. Lastly, the computed inverse filtering factor is then applied to the detected photoacoustic image to arrive at an image having greatly improved resolution.

13 Claims, 7 Drawing Sheets

METHOD AND APPARATUS FOR DETECTING PHOTOACOUSTIC SIGNAL

BACKGROUND OF THE INVENTION

This invention relates to a photoacoustic signal detecting method and apparatus utilizing a photoacoustic effect for the detection of surface and internal information of a sample and relates also to a method for detecting an internal defect of a semiconductor device.

The photoacoustic effect described above was discovered by Tyndall, Bell, Röntgen, et al. in 1881 and represents a phenomenon which will be described with reference to FIG. 1. That is, when, as shown in FIG. 1, an intensity-modulated laser beam (an intermittent laser beam) focused by a lens 5 irradiates a sample 7, heat is generated in a light absorption region Vop 21 inside the sample 7 and periodically diffuses through a thermal diffusion region Vth 23 determined by a thermal diffusion length $\mu_s$ 22 thereby inducing a thermal distortion wave, and this thermal distortion wave acts to generate a surface acoustic wave (an ultrasonic wave). Therefore, when this ultrasonic wave, that is, a photoacoustic signal, is detected by a microphone (an acousto-electrical transducer), a piezoelectric transducer element or an interferometer, and a signal component synchronous with the modulation frequency modulating the incident laser beam is then detected, surface and internal information of the sample can be detected. The above manner of detection of a photoacoustic signal is discussed in, for example, "HIHAKAI KENSA (Nondestructive Testing)" Vol. 36, No. 10, pp. 730-736 (Oct., 1987) and "IEEE; 1986 ULTRASONICS SYMPOSIUM", pp. 515-526, (1986). According to these publications, a photoacoustic signal generated as a result of irradiation of a sample with an intensity-modulated laser beam is detected by, for example, an interferometer so as to extract a frequency component synchronous with the modulation frequency modulating the incident laser beam. This extracted frequency component has surface or internal information of the sample corresponding to the modulation frequency. By changing the modulation frequency, the thermal diffusion length $\mu_s$ 21 shown in FIG. 1 can be changed, so that information in the direction of the depth of the sample can be obtained. Therefore, when a crack or any other defect is present inside the thermal diffusion region Vth 23 shown in FIG. 1, a signal level change appears in the extracted frequency component in the range of the interferometry intensity signal, so that the presence of the defect can be detected. However, although the prior art method described above is a very effective means capable of detecting the photoacoustic signal in a noncontact and nondestructive manner, the prior art method has had that difficulty in the case of detection of internal information of a sample having a microstructure of the order of a micron (1 μm) or less (submicron).

SUMMARY OF THE INVENTION

It is an object of the present invention to provide a photoacoustic signal detecting method and apparatus which minimizes unclear definition of a photoacoustic image, which greatly improves the resolution of the image and which can stably detect internal information of a sample with a high resolution of the order of a micron (1 μm) or less (submicron).

The present invention which attains the above object provides a photoacoustic signal detecting apparatus comprising a light source emitting a laser beam, modulating means for intensity-modulating the laser beam at a desired frequency, focusing means for focusing the intensity-modulated laser beam on a sample (for example, a semiconductor device) thereby inducing a photoacoustic effect inside the sample, detecting means for detecting the photoacoustic effect induced in the sample thereby generating a detection output signal, information extracting means for extracting surface and internal information of the sample from the detection output signal of the detecting means, and scanning means for two-dimensionally scanning the sample or scanning the laser beam from the the light source, in which a thermal impulse response of the sample (a transfer function representing the process in which a heat wave generated at an infinitely small point inside the sample propagates through the sample until it is converted into a minute displacement of the sample surface, that is, a photoacoustic signal) is computed so as to compute an inverse filtering factor used for compensating degradation of the resolution of a photoacoustic image on the basis of the computed thermal impulse response, and the computed inverse filtering factor is applied to the detected photoacoustic image, whereby the resolution of the photoacoustic image can be improved, and the internal information of the sample can be stably detected with a high resolution.

In another form of the photoacoustic signal detecting apparatus according to the present invention, a pure thermal impulse response in a homogeneous sample (a transfer function representing the process in which a heat wave generated at an infinitely small point inside the sample propagates through the sample until it is converted into an internal temperature distribution of the sample) and a thermoelastic impulse response (a transfer function representing the process in which a change in the temperature at the infinitely small point inside the sample is converted into a minute displacement of the sample surface, that is, a photoacoustic signal) are computed so as to compute an inverse filtering factor used for compensating degradation of the resolution of a detected photoacoustic image on the basis of the computed thermal and thermoelastic impulse responses, and the computed inverse filtering factor is applied to the detected photoacoustic image, whereby the resolution of the photoacoustic image can be improved, and the internal information of the sample can be stably detected with a high resolution.

When the range of the light absorption region Vop 21, that is, the area occupied by the spot diameter of the incident laser beam is narrower than the range of the thermal diffusion region Vth 23, the resolution of the photoacoustic signal in both the transverse (horizontal) and depthwise directions of the sample is given by the thermal diffusion length $\mu_s$ 22. This thermal diffusion length $\mu_s$ is defined by the following equation (1):

$$\mu_s = \sqrt{\frac{k}{\pi f \rho c}} \tag{1}$$

where,
k: thermal conductivity of sample
ρ: density of sample
c: specific heat of sample
f: intensity modulation frequency for laser beam When, for example, f=10 kHz, the value of $\mu_s$ in the case of Si or Al is of the order of 50 $\mu$m or less, while that of $\mu_s$ in the case of SiO$_2$ is of the order of 5 $\mu$m or less.

Suppose now that the internal information of the sample 7 is an internal thermal impedance distribution 7a of the sample 7 as shown in FIG. 2. As the sample 7 is continuously scanned with an exciting laser beam 19 (although, actually, the sample 7 is mounted on an XY stage to be moved relative to the scanning laser beam 19), both the amplitude and the phase of the thermal distortion wave change at successive beam positions due to the thermal impedance distribution 7a in the thermal diffusion region Vth 23 of the sample 7, and, as a result, a minute displacement 30 occurs on the surface of the sample 7. The photoacoustic signal is detected in the form of an interferometry intensity signal when the minute displacement 30 is detected by a probing laser beam 24 emitted from a laser in an interferometer. Therefore, the photoacoustic signal detected at each of the individual exciting laser beam positions is an integration of the thermal impedance information in the thermal diffusion region Vth 23. The photoacoustic signals obtained as a result of the integration of the thermal impedance information at the individual beam positions form a two-dimensional photoacoustic image. Accordingly, the photoacoustic image thus obtained tends to become the so-called unclearly defined image. A graph shown in the lower part of FIG. 2 represents the x-direction amplitude distribution p(x) of the photoacoustic image p(x,y) obtained by the integration of the thermal impedance distribution 7a shown in the upper part of FIG. 2. It will be seen from the graph that the signal portions at the x-direction boundaries of the thermal impedance distribution 7a are greatly smoothed.

This unclear definition of the photoacoustic image can be improved when the range of the thermal diffusion region Vth 23 is narrowed. However, it will be seen from the equation (1) that the thermal diffusion length $\mu_s$ is dependent on both the intensity modulation frequency f for the exciting laser beam 19 and the thermal properties of the sample 7. In order to limit the thermal diffusion length $\mu_s$ to the order of a micron (1 $\mu$m) or less (submicron), a modulation frequency of several hundred MHz is sometimes required depending on the sample. Therefore, when the factor such as the bandwidth of a lock-in amplifier is taken into consideration, it becomes very difficult at present to detect the internal information of a sample having a microstructure of the order of a micron (1 $\mu$m) or less (submicron).

Therefore, in another embodiment of the photoacoustic signal detecting apparatus according to the present invention, an inverse filtering factor is computed on the basis of both a pure thermal impulse response and a thermoelastic impulse response of a sample so as to compensate degradation of the resolution of a detected photoacoustic image, and the computed inverse filtering factor is applied to the detected photoacoustic image. Thus, the resolution of the photoacoustic image can be improved, and the internal information of the sample can be stably detected with a high resolution. That is, according to this embodiment of the present invention, the inverse filtering factor computed on the basis of both the pure thermal impulse response and the thermoelastic impulse response of the sample is applied to the detected photoacoustic image, so that degradation of the resolution of the photoacoustic image can be compensated, and the internal information of the sample can be stably detected with the high resolution.

DESCRIPTION OF THE PREFERRED EMBODIMENTS

Figure 1:
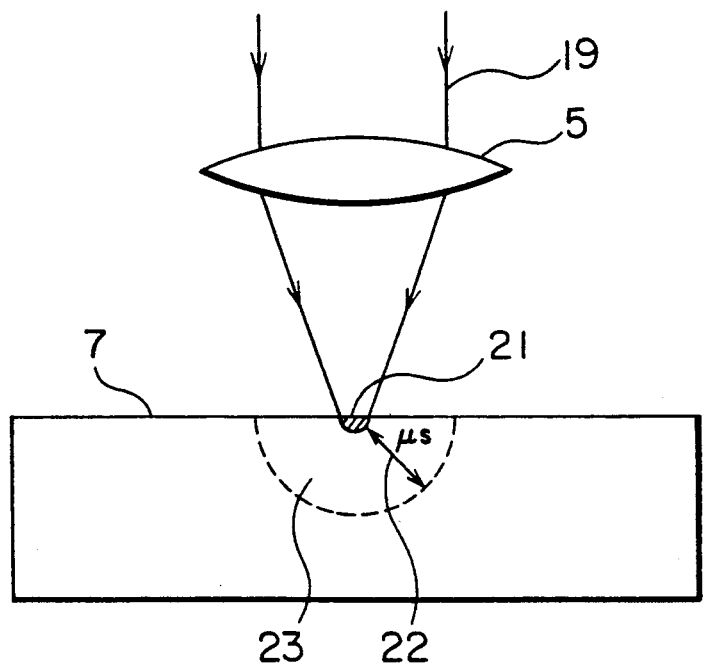
FIG. 1 illustrates the basic principle of the present invention.

Before describing the present invention in detail, its basic principle will now be described so that the present invention can be more clearly understood.

A photoacoustic image p(x,y) which will be actually detected is given by the following equation (2):

$$p(x,y) = \int \int_{-\mu_s}^{\mu_s} q(x - \epsilon, y - \eta) \cdot h(\epsilon,\eta) d\epsilon d\eta \quad (2)$$

where, $\mu_s$: thermal diffusion length q(x,y): ideal photoacoustic image This ideal photoacoustic image is provided by thermal impedance information detected at infinitely small points (=a set of infinitely small point heat sources) excited by a point light source moving on the surface of the sample.

h(x,y): thermal impulse response of sample This thermal impulse response is provided by a transfer function representing the process in which a heat wave generated at an infinitely small point inside the sample propagates through the sample until it is converted into a minute displacement of the sample surface, that is, a photoacoustic signal.

For example, h is expressed as follows:

$$h = \frac{\beta a l P}{2fpcA} \quad (3)$$

where,

β: coefficient of thermal expansion of sample
α: light absorption coefficient of sample
l: range of light absorption region Vop $\frac{P}{2f}$:

energy of incident laser beam in one cycle
ρ: density of sample
c: specific heat of sample
A: irradiated surface area of sample Generally, a photoacoustic signal is obtained in the form of a complex signal having an amplitude and a phase. The equation (2) is subjected to two-dimensional complex Fourier transformation to obtain the following equation (4):

$$P(\mu,\nu) = F[p(x,y)] \quad (4)$$
$$= Q(\mu,\nu)H(\mu,\nu)$$

where,

μ,ν: spatial frequencies in x- and y-direction respectively
P(μ,ν): Fourier transformed image of p(x,y)
Q(μ,ν): Fourier transformed image of q(x,y)
H(μ,ν): Fourier transformed image of h(x,y)

The term 1/H(μ,ν) is used as an inverse filtering factor, and both the left-hand and right-hand members of the equation (4) are multiplied by this factor to obtain the following equation (5):

$$Q(\mu,\nu) = P(\mu,\nu) \cdot \frac{1}{H(\mu,\nu)} \quad (5)$$

Then, when the equation (5) is subjected to two-dimensional inverse complex Fourier transformation, the ideal photoacoustic image q(x,y) is finally obtained as follows:

$$q(x,y) = F^{-1}[Q(\mu,\nu)] \quad (6)$$
$$= F^{-1}\left[P(\mu,\nu) \cdot \frac{1}{H(\mu,\nu)}\right]$$

Thus, when the inverse filtering factor 1/H(μ,ν) is computed on the basis of the thermal impulse response h(x,y) of the sample, and, after multiplying the Fourier transformed image P(μ,ν) of the detected photoacoustic image p(x,y) by the inverse filtering factor 1/H(μ,ν), the Fourier transformed image Q(μ,ν) is subjected to the inverse Fourier transformation, the ideal photoacoustic image q(x,y) free from degratation of the resolution can be obtained.

Preferred embodiments of the present invention will now be described in detail with reference to the drawings. In the above-mentioned field, a preceding U.S. Pat. application Ser. No 479712 was filed on Feb. 14, 1990, now U.S. Pat. No. 5,062,715, on behalf of the assignee of the present application and entitled as "Method and apparatus for detecting photoacoustic signal and method for detecting internal defect of semiconductor device" and assigned to the same assignee.

EMBODIMENT 1

Figure 3:
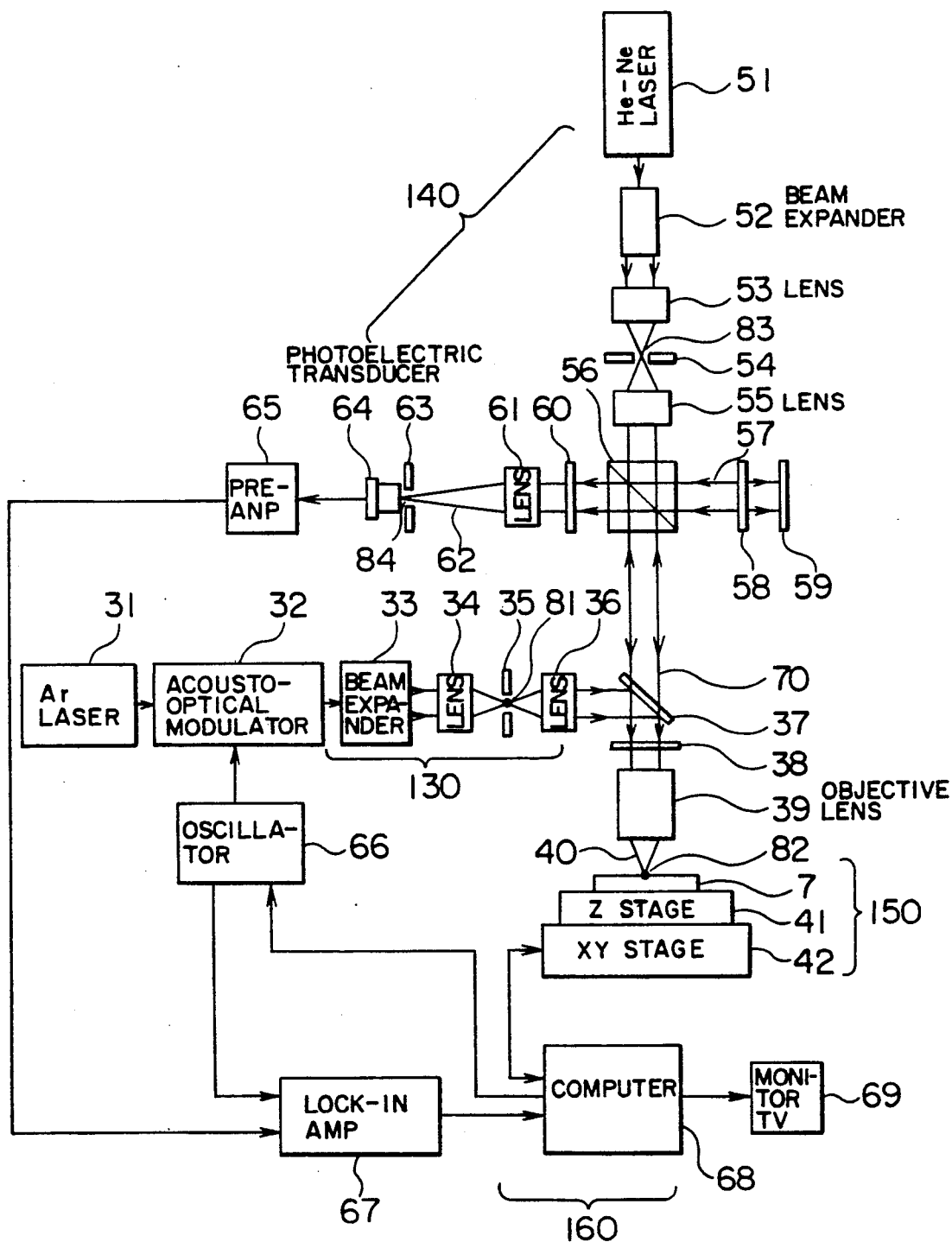
FIG. 3 is a block diagram showing the structure of the photoacoustic signal detecting optical system in a first embodiment of the photoacoustic signal detecting apparatus according to the present invention.

A first embodiment of the present invention will now be described with reference to FIGS. 3 to 8. FIG. 3 is a block diagram showing the structure of the photoacoustic signal detecting optical system in the first embodiment of the present invention. The illustrated optical system includes a modulated laser beam irradiation optical system 130 in which an Ar laser 31 emitting a parallel laser beam having a wavelength of 0.515 μm is used as a light source so as to induce the photoacoustic effect, a Michelson interferometer optical system 140 for detecting a photoacoustic signal, a stage system 150, and a signal processing system 160.

Figure 4:
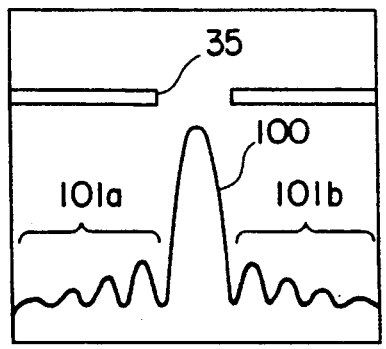
FIG. 4 illustrates how higher-order diffracted components of the laser beam spot are intercepted by the pin-hole shown in FIG. 3.
Figure 5:
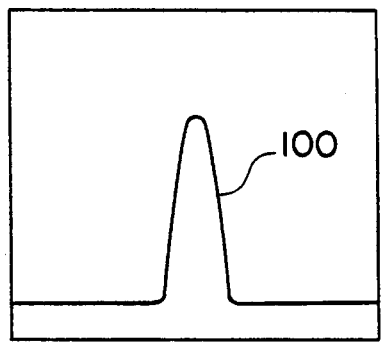
FIG. 5 shows the intensity distribution of the laser beam spot immediately after the laser beam spot passes through the pin-hole shown in FIG. 4.

In the modulated laser beam irradiation optical system 130, the parallel laser beam emitted from the Ar laser 31 is intensity-modulated by an acousto-optical modulation element 32 at a desired frequency to be turned into an intermittent laser beam. After the beam diameter of the intermittent laser beam is expanded to a desired value by a beam expander 33, the laser beam is focused by a lens 34 on the rear focal point 81 of the lens 34. A pin-hole 35 is located at this focal point 81, so that higher-order diffracted beam components 101a and 101b existing around the peak component 100 of the focused beam spot are shaded or intercepted by the pin-hole 35 as shown in FIG. 4. As a result, the peak component 100 only of the beam intensity distribution of the focused beam spot can pass through the pin-hole 35 as shown in FIG. 5. The rear focal point 81 of the lens 34 is located at the front focal point of a lens 36, and the laser beam spot passed through the pin-hole 35 is turned into the parallel laser beam again after it passes through the lens 36. A dichroic mirror 37 reflects a laser beam having a wavelength shorter than 0.58 μm but permits penetration of a laser beam having a wavelength longer than 0.6 μm. Therefore, the parallel laser beam appearing from the lens 36 is reflected by the dichroic mirror 37 and, after passing through a quarter wave plate 38, focused by an objective lens 39 on the front focal point 82 of the lens 39, so that the focused beam spot has the same beam intensity distribution as that shown in FIG. 5. A sample 7 is disposed at the front focal point 82 of the objective lens 39. Thus, the front focal point 81 of the lens 36 and the front focal point 82 of the objective lens 39 are conjugate and confocal relative to each other. The sample 7 is mounted on a Z stage 41 mounted on an XY stage 42 in the stage system 150.

Due to the photoacoustic effect, a thermal distortion wave is induced at the position 82 where the laser beam spot is focused on the surface of the sample 7, that is, at the front focal point 82 of the objective lens 39. Due to this thermal distortion wave, an ultrasonic wave is produced, and, at the same time, a minute displacement occurs on the surface of the sample 7.

The Michelson interferometer optical system 140 includes a He-Ne laser 51 which emits a circularly-polarized parallel laser beam having a wavelength of 0.633 μm. After the beam diameter of this circularly-polarized parallel laser beam is expanded to a desired value by a beam expander 52, the laser beam is focused by a lens 53 on the rear focal point 83 of the lens 53. A pin-hole 54 is located at this focal point 83, so that higher-order diffracted beam components around the peak component of the focused beam spot are shaded or intercepted in a manner similar to that described already with reference to FIG. 4. The rear focal point 83 of the lens 53 coincides with the front focal point of a lens 55, so that the laser beam spot passed through the pin-hole 54 is turned into the parallel laser beam again by the lens 55. This parallel laser beam is then split into a P-polarized laser beam and an S-polarized laser beam by a polarized beam splitter 56. The P-polarized laser beam penetrates the polarized beam splitter 56 and passes than through the dichroic mirror 37 and the quarter wave plate 38 to appear as the circularly-polarized laser beam again from the quarter wave plate 38. This circularly-polarized laser beam is focused by the objective lens 39 on the position 82 (the position of the front focal point of the objective lens 39) on the surface of the sample 7, so that the focused beam spot has its intensity distribution similar to that shown in FIG. 5. On the other hand, the S-polarized laser beam is reflected by the beam splitter 56 and passes then through a quarter wave plate 58 to be turned into the circularly-polarized laser beam which is incident on a reference mirror 59. The reflected laser beam from the sample 7 contains, as phase information, the minute displacement occurred on the surface of the sample 7. This reflected laser beam passes through the objective lens 39 and then through the quarter wave plate 38 to be turned into the S-polarized laser beam again, and this S-polarized laser beam is reflected by the polarized beam splitter 56. The reflected laser beam from the reference mirror 59 passes through the quarter wave plate 58 to be turned into the P-polarized laser beam again, and this P-polarized laser beam penetrates the polarized beam splitter 56.

Figure 6:
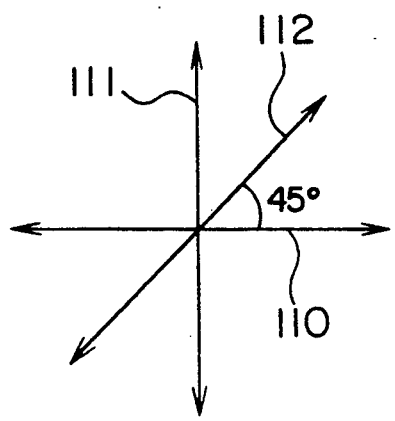
FIG. 6 illustrates the direction of beam polarization by the polarizer shown in FIG. 3.
Figure 7:
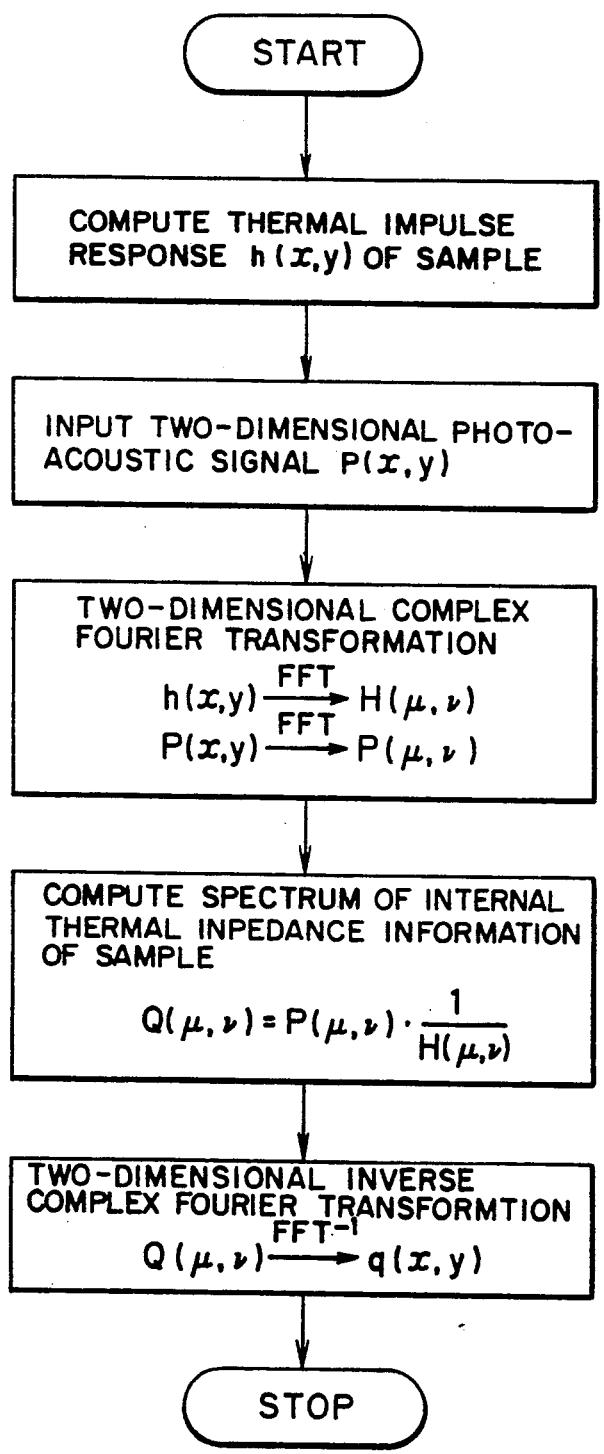
FIG. 7 is a flow chart showing the steps in which an inverse filtering factor is computed and used to compensate degradation of the resolution of a photoacoustic image.

In FIG. 6, the direction of polarization of the reflected laser beam from the sample 7 is indicated by the numeral 110, while the direction of polarization of the reflected laser beam from the reference mirror 59 is indicated by the numeral 111. It will be seen in FIG. 6 that these directions of polarization 110 and 111 are orthogonal with respect to each other, and the reflected laser beams do not interfere with each other when the relation between them is as shown. Therefore, a polarizer 60 is inserted in the optical path so as to provide a direction of polarization of 45° as indicated by the numeral 112 in FIG. 6, so that these two reflected laser beams now interfere with each other. In the beam interference pattern thus obtained, the minute displacement occurred on the surface of the sample 7 is contained as beam intensity information. The resultant laser beam is focused by a lens 61 on the rear focal point 84 of the lens 61, and the focused laser beam spot is detected by a photoelectric transducer 64 such as a photo diode to appear as an interferometry intensity signal. Also, a pinhole 63 is located at the rear focal point 84 of the lens 61, so as to shade or intercept stray beam components generated in the objective lens 39, multiple interference beam components generated in a transparent thin film forming part of the sample 7 and/or higher-order diffracted beam components generated due to minute irregularity of the surface of the sample 7.

In the Michelson interferometer optical system 140 described above, the front focal point 84 of the lens 61, the front focal point 82 of the objective lens 39 and the rear focal point 83 of the lens 53 are conjugate and confocal relative to one another. The interferometry intensity signal appearing from the photoelectric transducer 64 is applied to a lock-in amplifier 67 in the signal processing system 160 after being amplified by a preamplifier 65. In the lock-in amplifier 67, the modulation frequency signal generated from an oscillator 66 for driving the acousto-optical modulator 32 is used as a reference signal so as to extract the amplitude of the modulation frequency component included in the interferometry intensity signal as well as the phase component relative to the modulation frequency signal. The extracted frequency component and phase component contain the internal information of the thermal diffusion region Vth defined by the modulation frequency. Therefore, when this thermal diffusion region Vth includes a crack or any other defect or a region having a different thermal impedance, a change occurs in both the amplitude and the phase of the modulation frequency component included in the interferometry intensity signal, so that the presence of such a defect and such a region having a different thermal impedance can be detected.

The signal processing system 160 includes a computer 68 connected to the lock-in amplifier 67. The computer 68 executes processing of the detected photoacoustic image p(x,y) according to a flow chart shown in FIG. 7. In the first step, the thermal impulse response h(x,y) of the sample 7 is computed as $h(x,y) = hS(x,y)$, where h is given by equation (3) and S(x,y) represents the internal temperature distribution according to the description of equation (7). In the second step, the signal indicative of the movement of the XY stage 42 and the output signal of the lock-in amplifier 67 are applied to the computer 68 to compose the two-dimensional photoacoustic image p(x,y). In the third step, the thermal impulse response h(x,y) and the photoacoustic image p(x,y) are subjected to the two-dimensional complex Fourier transformation to provide their Fourier transformed images $H(\mu,\nu)$ and $P(\mu,\nu)$ respectively. In the fourth step, the inverse filtering factor $1/H(\mu,\nu)$ is computed, and, according to the equation (5), the spectrum of the internal thermal impedance information of the sample, that is, the Fourier transformed image $Q(\mu\nu)$ of the ideal photoacoustic image is obtained. In the final step, the Fourier transformed image $Q(\mu,\nu)$ is subjected to the two-dimensional inverse complex Fourier transformation according to the equation (6) to obtain the ideal photoacoustic image q(x,y). This ideal photoacoustic image q(x,y) is then displayed on a monitor TV set 69 connected to the computer 68.

Figure 2:
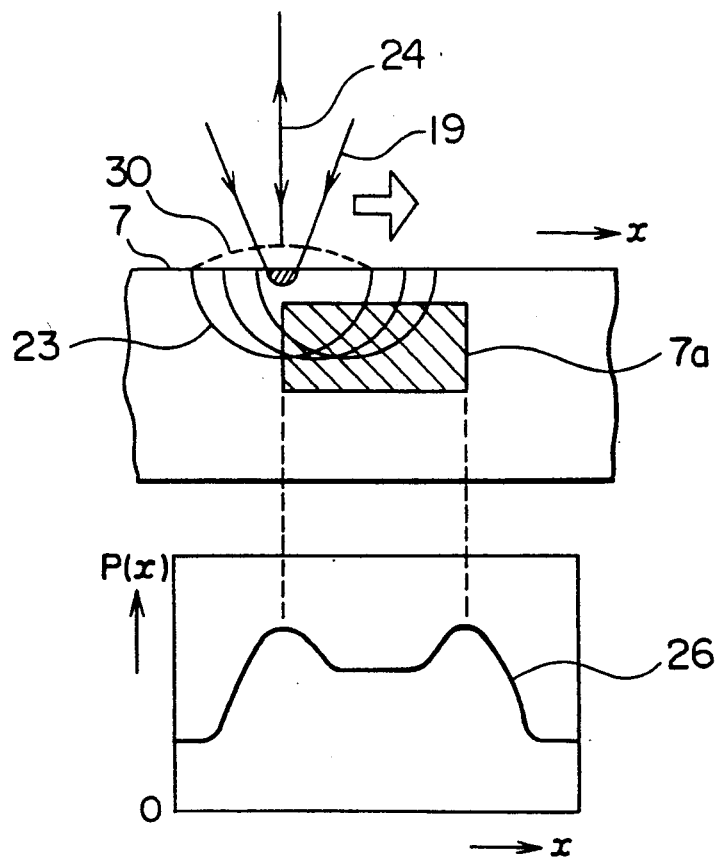
FIG. 2 illustrates how the resolution of a photoacoustic image is degraded due to the effect of integration in the thermal diffusion region of the sample shown in FIG. 1.
Figure 8:
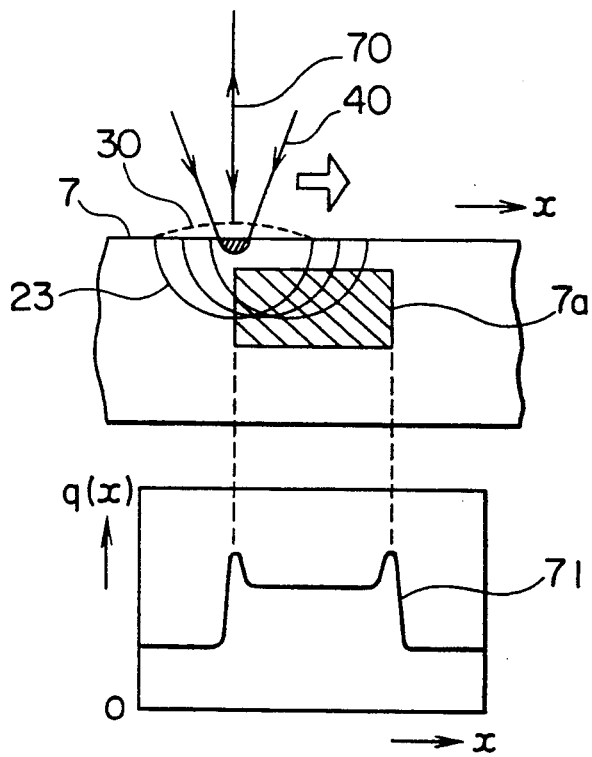
FIG. 8 illustrates the effect of the inverse filtering factor used in the present invention.

FIG. 8 shows, in its upper part, how the inverse filtering factor $1/H(\mu,\nu)$ is effective for providing the ideal photoacoustic image q(x,y) of the internal thermal impedance distribution 7a of the sample 7. A graph shown in the lower part of FIG. 8 represents the x-direction amplitude distribution q(x) of the ideal photoacoustic image q(x,y). It can be seen, from comparison with the graph shown in FIG. 2 representing the x-direction thermal impedance distribution obtained with the prior art method, that the signal portions at the x-direction boundaries of the thermal impedance distribution 7a are sharpened and clearly defined.

It will be understood from the above description of the first embodiment that an inverse filtering factor obtained by computation on the basis of a thermal impulse response of a sample is applied to a detected photoacoustic image of the sample, so that undesirable degradation of the resolution of the photoacoustic image can be compensated, and the internal information of the sample can be detected with a high resolution. Also, employment of an intensity-modulated laser irradiation optical system of confocal type is advantageous in that a minute laser beam spot free from the presence of peripheral higher-order diffracted beam components can be directed to irradiate the sample, and generation of noise components including stray beam components and the like can be minimized. Further, employment of a Michelson interferometer optical system of confocal type is also advantageous in that the adverse effects of interferometry beam components including stray beam components and beam components generated in the transparent film forming part of the sample as well as higher-order diffracted beam components generated due to minute surface irregularity of the sample can be substantially eliminated. Therefore, the sensitivity of detection of the photoacoustic signal, that is, the interferometry intensity signal, as well as the S/N ratio can be improved.

EMBODIMENT 2

Figure 9:
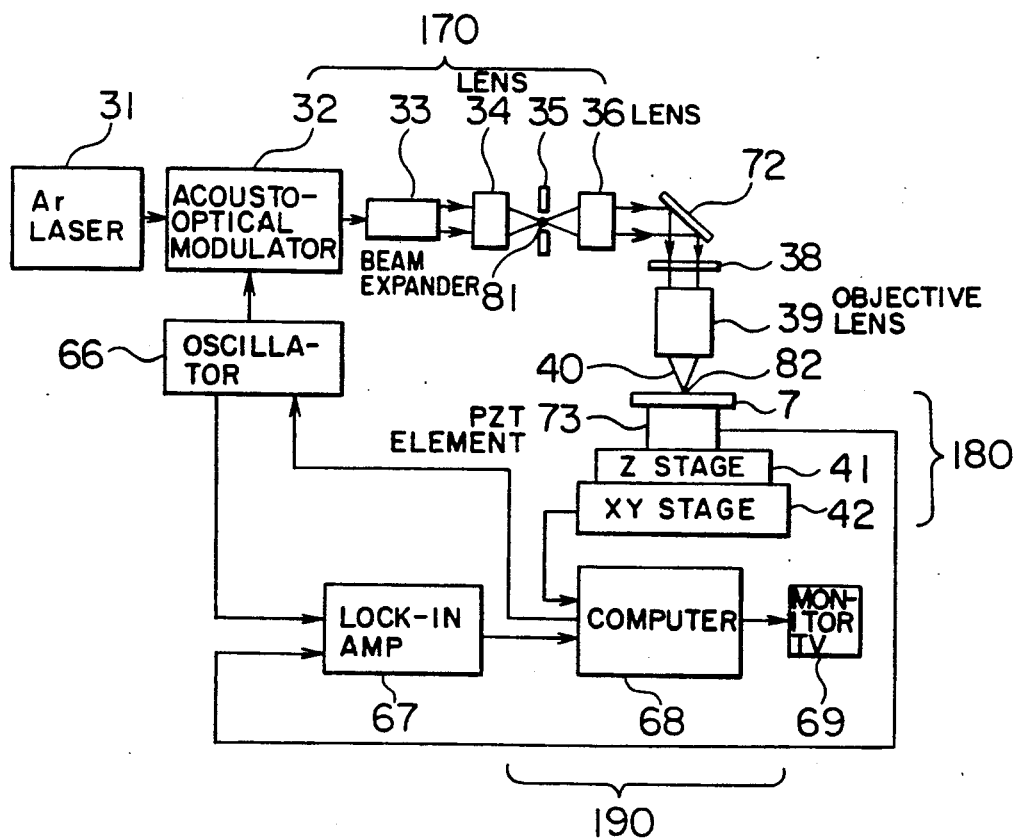
FIG. 9 is a block diagram showing the structure of the photoacoustic signal detecting optical system in a second embodiment of the present invention.

A second embodiment of the present invention will now be described with reference to FIG. 9. FIG. 9 shows the structure of the photoacoustic signal detecting optical system of the second embodiment. In this second embodiment, a PZT (piezoelectric transducer) element 73 is used in lieu of the Michelson interferometer optical system 140 shown in FIG. 3. The functions of an intensity-modulated laser irradiation optical system 170, a stage system 180 and a signal processing system 190 shown in FIG. 9 are entirely similar to those of the respective systems 130, 150 and 160 shown in FIG. 3, and any detailed description of the functions of such systems will not be specifically made herein.

It is apparent that this second embodiment is as effective as the first embodiment. Also, because the interferometer optical system is unnecessary, the overall arrangement of the photoacoustic signal detecting optical system can be made more compact thereby improving the stability of the operation.

EMBODIMENT 3

A third embodiment of the present invention will now be described with reference to FIGS. 10 and 11. In this third embodiment, the structure of its photoacoustic signal detecting optical system is entirely similar to that of the photoacoustic signal detecting optical system of the first embodiment shown in FIG. 3. Therefore, the photoacoustic signal detecting optical system in this third embodiment will not be specifically shown and described.

Figure 10:
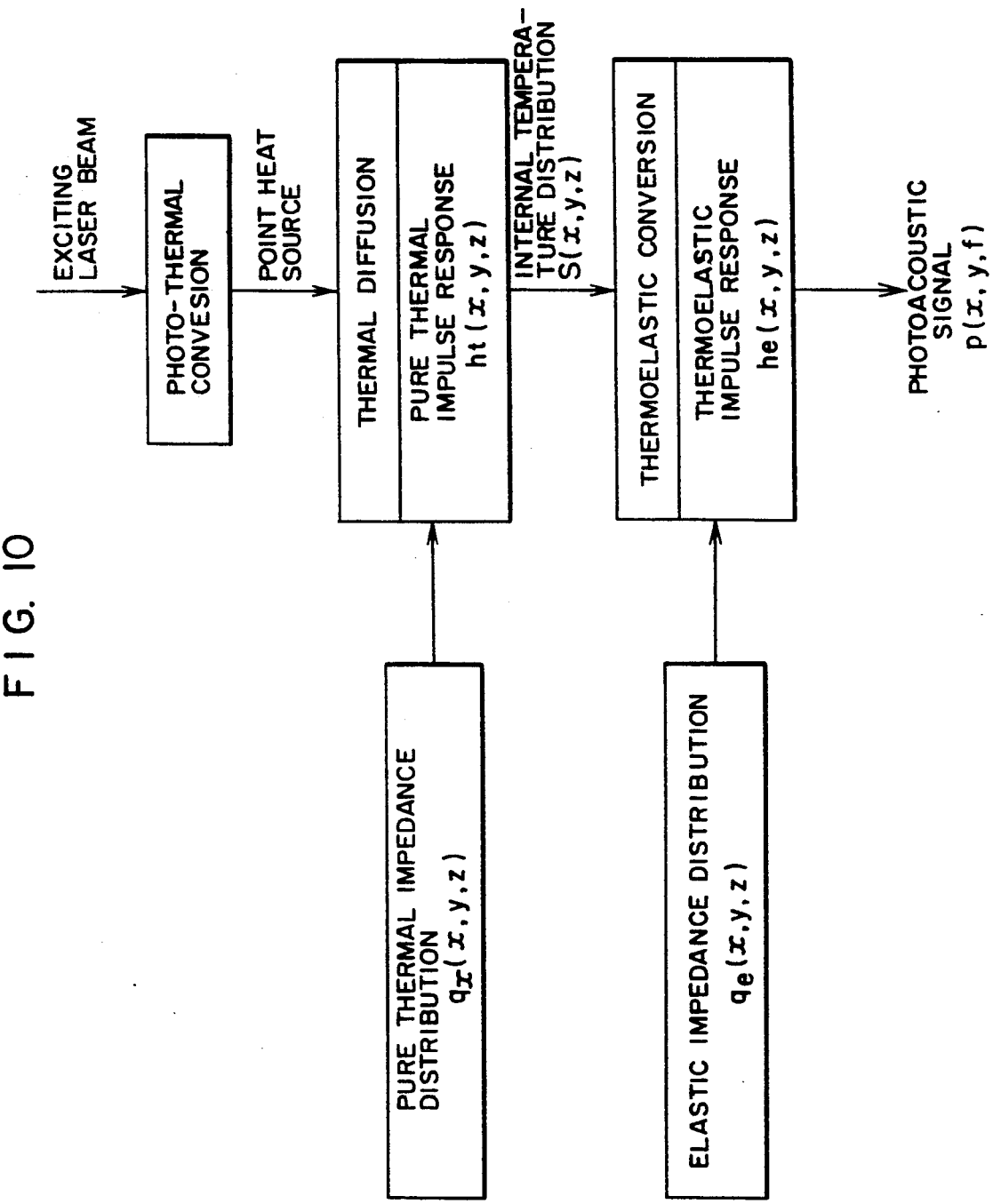
FIG. 10 illustrates the basic principle of a third embodiment of the present invention.

FIG. 10 illustrates the basic principle of this third embodiment. In the first and second embodiments described already, the thermal impedance distribution is presumed to be the principal factor representative of the internal information of the sample, and the frequency for intensity-modulating the laser beam irradiating the sample is maintained constant. This third embodiment differs from the first and second embodiments in that an elastic impedance distribution in addition to the thermal impedance distribution is considered to represent the internal information of a sample, and a detected photoacoustic image is handled as a function of the modulation frequency f, that is, a function pertaining to internal information in the direction of the depth of the sample. More precisely, as shown in FIG. 10, the exciting laser beam incident on the sample acts to provide a point heat source through a photo-thermal conversion process, and a heat wave from that point heat source propagates through the thermal diffusion region Vth of the sample to produce an internal temperature distribution $s(x,y,z)$ of the sample. Suppose that the above process is expressed in terms of a pure thermal impulse response $h_t(x,y,z)$, and the internal thermal impedance distribution of the sample is expressed as $q_t(x,y,z)$. Then, the internal temperature distribution $s(x,y,z)$ is approximately given by the following equation (7):

$$S(x,y,z) = \int \int \int_{-\mu_s}^{\mu_s} q_t(x-\epsilon, y-\eta, z-\tau) \cdot h_t(\epsilon,\eta,\tau) f \epsilon d\eta d\tau \quad (7)$$

where, $q_t(x,y,z)$: pure thermal impedance distribution = ideal photoacoustic image $h_t(x,y,z)$: pure thermal impulse This pure thermal impulse response is provided by a transfer function representing the process in which a heat wave generated at an infinitely small point inside the sample propagates through the sample until it is converted into an internal temperature distribution.

In FIG. 10, the internal temperature distribution $s(x,y,z)$ is then modulated by an elastic impedance distribution $q_e(x,y,z)$ and thermoelastically converted into an elastic or acoustic wave representing a thermoelastic impulse response $h_e(x,y,z)$ of the sample. This thermoelastic impulse response $h_e(x,y,z)$ is finally converted into a photoacoustic signal $p(x,y,f)$. This process is expressed as a function of the thermoelastic impulse response $h_e(x,y,z)$ of the sample, and the photoacoustic signal $p(x,y,f)$ is given by the following equation (8):

$$P(x,y,f) = \int \int \int_{-\mu_s}^{\mu_s} S_q(x-\epsilon, y-\eta, z-\tau) \cdot h_e(\epsilon,\eta,\tau) f \epsilon d\eta d\tau \quad (8)$$

where, $$s_q(x,y,z) = q_e(x,y,z) \cdot s(x,y,z) \quad (9)$$

$q(x,y,z)$: elastic impedance distribution = ideal photoacoustic image $h_e(x,y,z)$: thermoelastic impulse response This thermoelastic impulse response is provided by a transfer function representing the process in which a change in the temperature at an infinitely small point inside the sample is converted into a minute displacement of the sample surface, that is, a photoacoustic signal.

Generally, the photoacoustic signal is obtained in the form of a complex signal having an amplitude and a phase. Therefore, the equations (7), (8) and (9) are subjected to three-dimensional complex Fourier transformation to obtain the following equations (10), (11) and (12):

$$S(\mu,\nu,\gamma) = F[s(x,y,z)] \quad (10)$$
$$= Q_t(\mu,\nu,\gamma) \cdot H_t(\mu,\nu,\gamma)$$
$$P(\mu,\nu,\delta) = S_q(\mu,\nu,\gamma) \cdot H_e(\mu,\nu,\gamma) \quad (11)$$
$$S_q(\mu,\nu,\gamma) = Q_e(\mu,\nu,\gamma) \otimes S(\mu,\nu,\gamma) \quad (12)$$

where,

F[ ]: operator indicating Fourier transformation
$\otimes$: operator indicating convolution
$\mu,\nu,\gamma$: x-, y- and z-direction spatial frequencies
$\delta$: z-direction spatial frequency
$S(\mu,\nu,\gamma)$: Fourier transformed image of $s(x,y,z)$
$Q_t(\mu,\nu,\gamma)$: Fourier transformed image of $q_t(x,y,z)$
$H_t(\mu,\nu,\gamma)$: Fourier transformed image of $h_t(x,y,z)$
$P(\mu,\nu,\delta)$: Fourier transformed image of $p(x,y,f)$ $S_q(\mu,\nu,\gamma)$: Fourier transformed image of $s_q(x,y,z)$
$H_e(\mu,\nu,\gamma)$: Fourier transformed image of $h_e(x,y,z)$
$Q_e(\mu,\nu,\gamma)$: Fourier transformed image of $q_e(x,y,z)$ Substitution of the equations (10) and (12) into the equation (11) provides the following equation (13):

$$P(\mu,\nu,\delta) = Q_e(\mu,\nu,\gamma) \otimes Q_t(\mu,\nu,\gamma) \cdot H_t(\mu,\nu,\gamma) \cdot H_e(\mu,\nu,\gamma) \quad (13)$$

Therefore, when $1/\{H_t(\mu,\nu,\gamma) \cdot H_e(\mu,\nu,\gamma)\}$ is used as an inverse filtering factor, and both the left-hand and right-hand members of the equation (13) are multiplied by this inverse filtering factor, the following equation (14) is obtained:

$$Q_e(\mu,\nu,\gamma) \otimes Q_t(\mu,\nu,\gamma) = P(\mu,\nu,\delta) \cdot \frac{1}{H_t(\mu,\nu,\gamma) \cdot H_e(\mu,\nu,\gamma)} \quad (14)$$

Then, when the equation (14) is subjected to three-dimensional inverse complex Fourier transformation, the product of the thermal impedance distribution $q_t(x,y,z)$ and the elastic impedance distribution $q_e(x,y,z)$ provides the ideal photoacoustic image as follows:

$$\begin{aligned} q_e(x,y,z) \cdot q_t(x,y,z) &= F^{-1}[Q_e(\mu,\nu,\gamma) \otimes Q_t(\mu,\nu,\gamma)] \\ &= F^{-1}\left[ P(\mu,\nu,\delta) \cdot \frac{1}{H_t(\mu,\nu,\gamma) \cdot H_e(\mu,\nu,\gamma)} \right] \end{aligned} \quad (15)$$

Thus, an ideal photoacoustic image free from degradation of the resolution is obtained by computing inverse filtering factor $1/\{H_t(\mu,\nu,\gamma) \cdot H_e(\mu,\nu,\gamma)\}$ on the basis of the pure thermal impulse response $h_t(x,y,z)$ and the thermoelastic impulse response $h_e(x,y,z)$ of the sample, multiplying the Fourier transformed image $P(\mu,\nu,\delta)$ of the detected photoacoustic image $p(x,y,f)$ by the inverse filtering factor and then subjecting the result of multiplication to the inverse Fourier transformation.

The structure and function of the photoacoustic signal detecting optical system in this third embodiment are entirely the same as those of the optical system of the first embodiment, and any detailed description of the structure and function of the optical system will not be specifically described herein.

Figure 11:
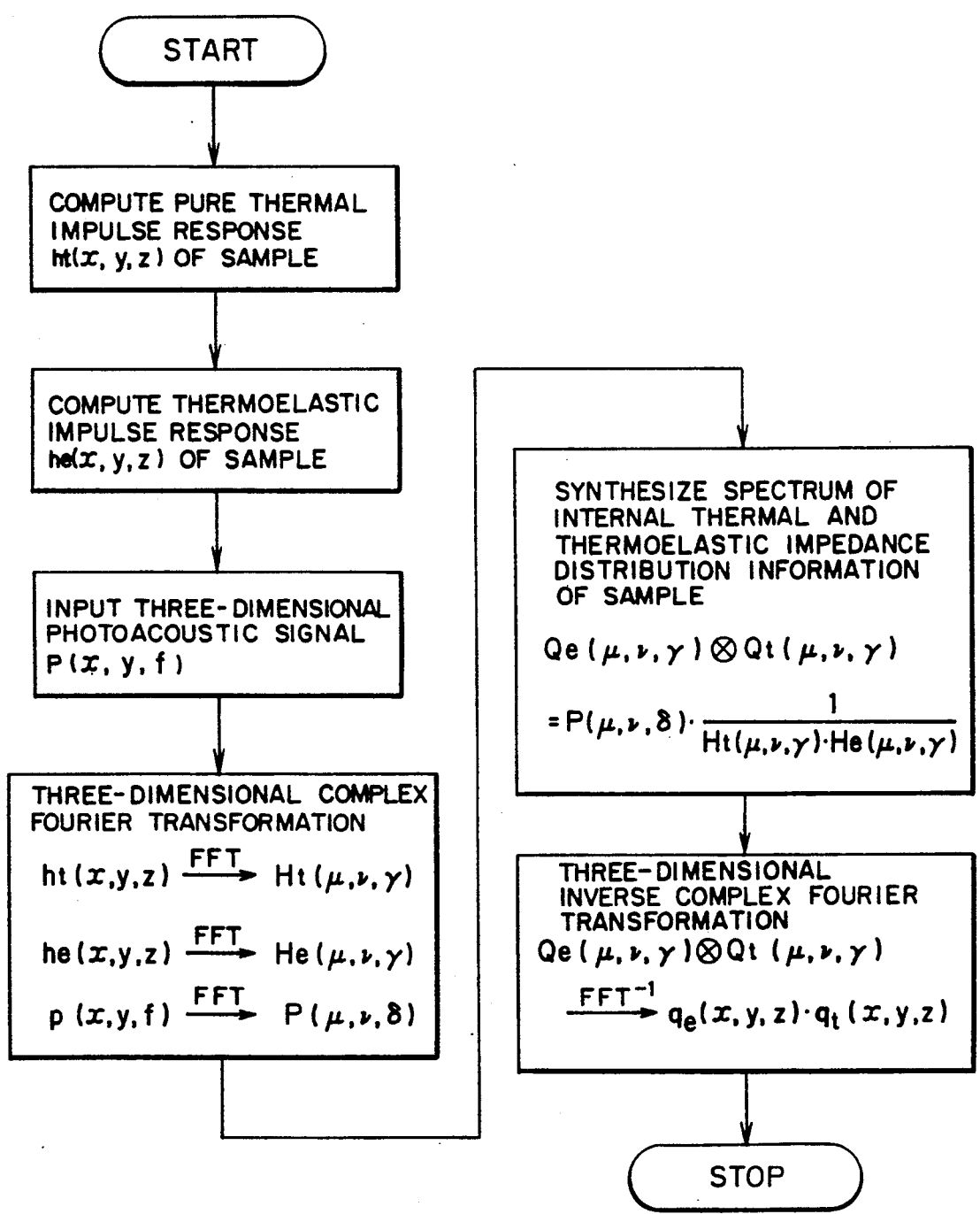
FIG. 11 is a flow chart showing the steps in which the inverse filtering factor is used in the third embodiment so as to compensate degradation of the resolution of a photoacoustic image.

The computer 68 in the signal processing system 160 executes processing of the detected photoacoustic image $p(x,y,f)$ according to a flow chart shown in FIG. 11. In the first and second steps, the thermal impulse response $h_t(x,y,z)$ and the thermoelastic impulse response $h_e(x,y,z)$ of the sample are computed on the basis of the various physical constants of the thermal and elastic properties of the sample. In the third step, the signal indicative of the movement of the XY stage 42 and the output signal of the lock-in amplifier 67 are applied to the computer 68 while scanning the modulation frequency f so as to form a three-dimensional photoacoustic image $p(x,y,f)$. In the fourth step, the thermal impulse response $h_t(x,y,z)$, the thermoelastic impulse response $h_e(x,y,z)$ and the photoacoustic image $p(x,y,f)$ are subjected to three-dimensional complex Fourier transformation to provide their Fourier transformed images $H_t(\mu,\nu,\gamma)$, $H_e(\mu,\nu,\gamma)$ and $P(\mu,\nu,\gamma)$ respectively. In the fifth step, after computing the inverse filtering factor $1/\{(H_t(\mu,\nu,\gamma) \cdot H_e(\mu,\nu,\gamma))\}$, the synthesized spectrum of the internal thermal impedance distribution information and the internal elastic impedance distribution information of the sample, that is, the Fourier transformed image $Q_e(\mu,\nu,\gamma) \otimes Q_t(\mu,\nu,\gamma)$ of the ideal photoacoustic image is obtained according to the equation (14). In the final step, the Fourier transformed image $Q_e(\mu,\nu,\gamma) \otimes Q_t(\mu, \nu,\gamma)$ is subjected to the three-dimensional inverse complex Fourier transformation according to the equation (15) to obtain the ideal photoacoustic image $q_e(x,y,z) \cdot q_t(x,y,z)$. This image is displayed on the monitor TV set 69.

This third embodiment is also as effective as the first embodiment in that the internal information of the sample can be detected with a high resolution. According to the third embodiment, the elastic impedance distribution information in addition to the thermal impedance distribution information can be also detected as the internal information of the sample. Also, when the inverse filtering factor is combined with the scanning of the modulation frequency f, the resolution in the depthwise direction of sample can be improved.

It will be understood from the foregoing detailed description of the present invention that an inverse filtering factor computed on the basis of a thermal impulse response and a thermoelastic impulse response of a sample is applied to a detected photoacoustic image so as to compensate undesirable degradation of the resolution of the photoacoustic image, so that internal information of the sample can be detected with a high resolution.

We claim:

1. A photoacoustic method for detecting two-dimensional information of a sample, the method comprising the steps of:

intensity-modulating a light beam emitted from a light source to provide an intensity-modulated beam having a desired frequency;

focusing said intensity-modulated beam on the sample thereby generating a thermal distortion due to a photoacoustic effect inside the sample and scanning the focused intensity-modulated beam over the sample within a plane in two-dimensional x-y directions in the plane;

detecting the thermal distortion due to the photoacoustic effect in the two-dimensional x-y directions of the sample using a transducer apparatus and composing a two-dimensional photoacoustic image $p(x,y)$ of the sample;

providing a two-dimensional thermal impulse response $h(x,y)$ of the sample comprising a two-dimensional transfer function representing a two-dimensional minute displacement of the sample surface generated by propagating a heat wave, generated at an infinitely small point inside the sample, through the sample;

calculating a two-dimensional complex Fourier transformed image $P(\mu,\nu)$ from said two-dimensional photoacoustic image $p(x,y)$ and a two-dimensional complex Fourier transformed image $H(\mu,\nu)$ from said two-dimensional thermal impulse response $h(x,y)$, $\mu,\nu$ being spatial frequencies in the x and y directions respectively and calculating an ideal two-dimensional photoacoustic image $q(x,y)$ by performing a two-dimensional inverse complex Fourier transformation in accordance with $$q(x,y) = F^{-1}\left[ P(\mu,\nu) \cdot \frac{1}{H(\mu,\nu)} \right]$$

by using said two-dimensional complex Fourier transformed image $P(\mu,\nu)$ and said two-dimensional complex Fourier transformed image $H(\mu,\nu)$, whereby said ideal two-dimensional photoacoustic image $q(x,y)$ is compensated for degradation of the resolution of said two-dimensional photoacoustic image $p(x,y)$; and extracting a two-dimensional modulated frequency component contained in said ideal two-dimensional photoacoustic image $q(x,y)$ calculated, by referencing said desired frequency modulating said light beam, whereby said two-dimensional information of the sample is detected in accordance with said two-dimensional modulated frequency component extracted.

2. The method according to claim 1, wherein said step of providing said two-dimensional thermal impulse response $h(x,y)$ of the sample comprises calculating $h \cdot S(x,y)$ according to:

$$h = \frac{\beta \alpha l P}{2fpcA}$$

where $\beta$ comprises a coefficient of thermal expansion of sample, $\alpha$ comprises a light absorption coefficient of sample, l comprises a range of light absorption region $V_{op}$, P/2f comprises the energy of said light beam in one cycle, $p$ comprises the density of said sample, c comprises the specific heat of said sample, A comprises an irradiated surface area of said sample, and $S(x,y)$ comprises a two-dimensional temperature distribution.

3. An apparatus for detecting a surface or internal two-dimensional information of a sample using a photoacoustic signal, the apparatus comprising:

a light source emitting a light beam;

modulating means for intensity-modulating the light beam emitted from said light source providing an intensity-modulated beam having a desired frequency;

focusing-scanning means for focusing said intensity-modulated beam on the sample thereby generating a thermal distortion in the sample due to a photoacoustic effect inside the sample and scanning the focused intensity-modulated beam over the sample in a surface in x and y directions in the surface;

detecting means for detecting the thermal distortion due to the photo-acoustic effect in two-dimensional directions of the sample and composing a two-dimensional photoacoustic image $p(x,y)$ of the surface of the sample;

impulse response providing means for providing a two-dimensional thermal impulse response $h(x,y)$ of the sample comprising a two-dimensional transfer function representing a two-dimensional minute displacement of the sample surface generated by propagating a heat wave, generated at an infinitely small point inside the sample, through the sample;

calculating means for calculating a two-dimensional complex Fourier transformed image $P(\mu,\nu)$ from said two-dimensional photoacoustic image $p(x,y)$ detected by said detecting means and a two-dimensional complex Fourier transformed image $H(\mu,\nu)$ from said two-dimensional thermal impulse response $h(x,y)$ provided by said impulse response providing means, $\mu$, $\nu$ being spacial frequencies in the x and y directions respectively and calculating an ideal two-dimensional photoacoustic image $q(x,y)$ by performing a two-dimensional inverse complex Fourier transformation in accordance with $$q(x,y) = F^{-1}\left[ P(\mu,\nu) \cdot \frac{1}{H(\mu,\nu)} \right]$$

by using said two-dimensional complex Fourier transformed image $P(\mu,\nu)$ and said two-dimensional Fourier image $H(\mu,\nu)$ calculated, whereby said ideal two-dimensional photoacoustic image $q(x,y)$ is resolution compensated for degradation of said two-dimensional photoacoustic image $p(x,y)$; and extracting means for extracting a two-dimensional modulated frequency component contained in said ideal two-dimensional photoacoustic image $q(x,y)$ calculated by said calculating means, by referencing said desired frequency modulating said light beams, whereby said surface or internal two-dimensional information of the sample is detected in accordance with said two-dimensional modulated frequency component extracted.

4. The apparatus according to claim 3, wherein said impulse response providing means comprises calculating means for calculating said two-dimensional thermal impulse response $h(x,y)$ of the sample in accordance with $h \cdot S(x,y)$ according to:

$$h = \frac{\beta \alpha l P}{2fpcA}$$

where $\beta$ comprises a coefficient of thermal expansion of sample, $\alpha$ comprises a light absorption coefficient of sample, l comprises a range of light absorption region $V_{op}$, P/2f comprises the energy of said light beam in one cycle, $p$ comprises the density of said sample, c comprises the specific heat of said sample, A comprises an irradiated surface area of said sample, and $S(x,y)$ comprises a two-dimensional temperature distribution.

5. A photoacoustic signal detecting method comprising the steps of:

intensity-modulating a light beam emitted from a light source to provide an intensity-modulated beam having a desired frequency;

focusing said intensity-modulated beam on a sample thereby inducing a photoacoustic effect inside the sample;

detecting the photoacoustic effect in three-dimensional directions of the sample so as to compose a three-dimensional photoacoustic image of the sample;

extracting surface and internal information of the sample from said three-dimensional photoacoustic image;

computing, on the basis of a pure thermal impulse response and a thermoelastic impulse response of the sample, an inverse filtering factor for compensating degradation of the resolution of said photoacoustic image, said thermoelastic impulse response of the sample representing an inherent characteristic property of the sample in which a change in temperature at an infinitely small point inside said sample is converted into a minute displacement of the sample surface; and applying said computed inverse filtering factor for said detected photoacoustic image.

6. A photoacoustic signal detecting method according to claim 5, wherein said pure thermal impulse response is provided by a transfer function representing the process in which a heat wave generated at an infinitely small point inside the sample propagates through the sample until it is converted into an internal temperature distribution of the sample.

7. A method for detecting surface or internal three-dimensional information of a sample through use of photoacoustic signal, the method comprising the steps of:

intensity-modulating a light beam emitted from a light source to provide a plurality of intensity-modulated beams obtained by changing frequency so that each of the intensity-modulated beams have a different desired frequency;

focusing each of said intensity-modulated beams on a sample in a first direction thereby generating thermal distortions due to photoacoustic effects inside the sample corresponding to each of different desired frequencies and scanning the focused intensity-modulated beams over the surface of said sample in second and third directions, the second and third directions being orthogonal to each other and to the first direction;

detecting each of the thermal distortions due to each of the photoacoustic effects in two-dimensional directions of the sample corresponding to each of different desired frequencies by an interferometer optical system so as to compose a three-dimensional photoacoustic image $p(x,y,f)$ of the surface of the sample;

providing a three-dimensional pure thermal impulse response $h_t(x,y,z)$ of the sample comprising a three-dimensional transfer function representing a three-dimensional internal temperature distribution generated by propagating a heat wave, generated at an infinitely small point inside the sample, through the sample and a three-dimensional thermoelastic impulse response $h_e(x,y,z)$ of the sample comprising a three-dimensional minute displacement of the sample surface generated in accordance with said three-dimensional internal temperature distribution;

calculating a three-dimensional complex Fourier transformed image $P(\mu,\nu,\delta)$ from said three dimensional photoacoustic image $p(x,y,f)$, a three-dimensional complex Fourier transformed image $H_t(\mu,\nu,\gamma)$ from said three-dimensional pure thermal impulse response $h_t(x,y,z)$ and a three-dimensional complex Fourier transformed $H_e(\mu,\nu,\gamma)$ from said three-dimensional thermoelastic impulse response $h_e(x,y,z)$, $\mu,\nu,\gamma,\delta$ being spatial frequencies in second (x), third (y), first (z) and first (−z) directions respectively and calculating an ideal three-dimensional acoustic image $q_e(x,y,z)\cdot q_t(x,y,z)$ by performing a three-dimensional inverse complex Fourier transformation in accordance with:

$$q_e(x,y,z)\cdot q_t(x,y,z) = F^{-1}\left[P(\mu,\nu,\delta)\cdot \frac{1}{H_t(\mu,\nu,\gamma)\cdot H_e(\mu,\nu,\gamma)}\right]$$

using said three-dimensional complex Fourier transformed image $P(\mu,\nu,\delta)$, said three-dimensional complex Fourier transformed image $H_t(\mu,\nu,\gamma)$ and said three-dimensional complex Fourier transformed image $H_e(\mu,\nu,\gamma)$ calculated, whereby said ideal three-dimensional photoacoustic image $q_e(x,y,z)\cdot q_t(x,y,z)$ is resolution compensated for degradation of said three-dimensional photoacoustic image $p(x,y,f)$ and, extracting a three-dimensional modulated frequency component corresponding to each of different desired frequencies contained in said ideal three-dimensional photoacoustic image $q_e(x,y,z)\cdot q_t(x,y,z)$ calculated by referencing each of said desired frequencies modulating said light beam, whereby the surface or internal three-dimensional information of the sample is detected in accordance with said three-dimensional modulated frequency component extracted.

8. An apparatus for detecting three-dimensional information of a sample using a photoacoustic signal comprising:

a light source emitting a light beam;

modulating means for intensity-modulating said light beam emitted rom said light source to provide a plurality of intensity-modulated beams obtained by changing frequency so that each of the intensity-modulated beams has a different desired frequency;

focusing means for focusing each of said intensity-modulated beams on the sample in a first direction (z) thereby generated thermal distortion due to photoacoustic effects inside the sample corresponding to each of different desired frequencies and scanning relatively the focused intensity-modulated beams over the sample in a second direction (x) and a third direction (y);

detecting means for detecting each of the thermal distortions due to each of the photoacoustic effects in two-dimensional directions of the sample corresponding to each of different desired frequencies by a transducer system so as to compose a three-dimensional photoacoustic image $p(x,y,f)$ of the surface of the sample;

impulse response providing means for providing i) a three-dimensional pure thermal impulse response $h_t(x,y,z)$ of the sample comprising a three-dimensional transfer function representing a three-dimensional internal temperature distribution generated by propagating a heat wave, generated at an infinitely small point inside the sample, through the sample and ii) a three-dimensional thermoelastic impulse response $h_e(x,y,z)$ of the sample comprising a three-dimensional transfer function representing a three-dimensional minute displacement of the sample surface generated in accordance with said three-dimensional internal temperature distribution;

calculating means for calculating a three-dimensional Fourier transformed image $P(\mu,\nu,\delta)$ from said three-dimensional photoacoustic image $p(x,y,f)$, a three-dimensional complex Fourier transformed image $H_t(\mu,\nu,\gamma)$ from said three-dimensional pure thermal response $h_t(x,y,z)$ and a three-dimensional complex Fourier transformed image $H_e(\mu,\nu,\gamma)$ from said three-dimensional thermoelastic impulse response $h_e(x,y,z)$, $\mu$, $\nu$, $\gamma$, $\delta$ being spatial frequencies in the second (x), third (y), first (z) and −first (−z) directions respectively and calculating an ideal three-dimensional photoacoustic image $q_e(x,y,z)\cdot q_r(x,y,z)$ by performing a three-dimensional inverse complex Fourier transformation in accordance with:

$$qe(x,y,z) \cdot qr(x,y,z) = F^{-1}\left[ P(\mu,\nu,\delta) \cdot \frac{1}{Hr(\mu,\nu,\gamma) \cdot He(\mu,\nu,\gamma)} \right]$$

using said three dimensional complex Fourier transformed image $P(\mu,\nu,\delta)$, said three-dimensional complex Fourier transformed image $H_r(\mu,\nu,\gamma)$ and said three-dimensional complex Fourier transformed image $H_e(\mu,\nu,\gamma)$ calculated, whereby said three-dimensional photoacoustic image $q_e(x,y,z)/q_r(x,y,z)$ is resolution compensated for degradation of said three-dimensional photoacoustic image $p(x,y,f)$ and dimensional photoacoustic image $p(x,y,f)$ and, extracting means for extracting a three-dimensional modulated frequency component corresponding to each of different desired frequencies contained in said ideal three-dimensional photoacoustic image $q_e(x,y,z)\cdot q_r(x,y,z)$ calculated by said calculating means, by referencing each of said desired frequencies modulating said light beam, whereby the three-dimensional information of the sample is detected in accordance with said three-dimensional modulated frequency component extracted by said extracting means.

9. The apparatus according to claim 8, wherein said impulse response providing means comprises calculating means.

10. The apparatus according to claim 8, wherein said focusing means comprises first confocal optical means to converge said intensity-modulated excitation light into a fine intensity-modulated excitation light spot on the sample surface and first removing means for removing high order diffraction light components around said fine intensity-modulated excitation light spot.

11. The apparatus according to claim 3, wherein said focusing means comprises first confocal optical means to converge said intensity-modulated excitation light into a fine intensity-modulated excitation light spot on the sample surface and first removing means for removing high order diffraction light components around said fine intensity-modulated excitation light spot.

12. The apparatus according to claim 3, wherein said detecting means comprises light interference detection means for detecting an interference intensity signal caused by said generated thermal distortion, said light interference detection means comprising an interference light source means or emitting an interference light, a second confocal optical means for irradiating the sample surface by converging the interference light into a fine interference light spot whereby the fine interference light spot and the intensity-modulated excitation file light spot substantially occupy the same sample surface position, second removing means for removing high order diffraction light spot, and an optical detection means for detecting a focused interfered light that is reflected from the irradiated sample surface and which contains the interference intensity signal, said optical detection means including a third removing means for removing high order light diffraction components from the focused interfered light.

13. The apparatus according to claim 8, wherein said detecting means comprises light interference detection means for detecting an interference intensity signal caused by said generated thermal distortion, said light interference detection means comprising an interference light source means for emitting an interference light, a second confocal optical means for irradiation the sample surface by converging the interference light into a fine interference light spot whereby the fine interference light spot and the intensity-modulated excitation fine light spot substantially occupy the same sample surface position, second removing means for removing high order diffraction light components around said fine interference light spot, and an optical detection means for detecting a focused interfered light that is reflected from the irradiated sample surface and which contains the interference intensity signal, said optical detection means including a third removing means for removing high order diffraction components from the focused interfered light.

* * * * *

UNITED STATES PATENT AND TRADEMARK OFFICE
CERTIFICATE OF CORRECTION

PATENT NO. : 5,136,172
DATED : August 4, 1992
INVENTOR(S) : Toshihiko Nakata, et al.

It is certified that error appears in the above-identified patent and that said Letters Patent is hereby corrected as shown below:

Claim 3, column 14, line 17, delete "beams" and replace with --beam--.

Claim 8, column 16, line 25, delete "rom" and replace with --from--.

Claim 8, column 16, line 31, delete "generated" and replace with --generating--.

Claim 8, column 16, line 31, delete "distortion" and replace with --distortions--.

Claim 8, column 17, lines 11 and 12, delete "$q_e(x-,y,z)/q_t(x,y,z)$" and replace with --$q_e(x,y,z) \cdot q_t(x,y,z)$--.

Claim 12, column 18, line 16, after "diffraction" insert --light components around said fine interference--.

Claim 13, column 18, line 29, delete "irradiation" and replace with --irradiating--.

Signed and Sealed this

Tenth Day of August, 1993

Attest:

MICHAEL K. KIRK

*Attesting Officer*  Acting Commissioner of Patents and Trademarks